United States Patent
Speak (10) Patent No.: US 10,016,318 B2
(45) Date of Patent: Jul. 10, 2018

(54) ABSORBENT ARTICLE WITH A BACTERIAL ISOLATION PAD AND HYGIENIC GRIPPING TABS

(71) Applicant: Jane Speak, Tequesta, FL (US)

(72) Inventor: Jane Speak, Tequesta, FL (US)

( * ) Notice: Subject to any disclaimer, the term of this patent is extended or adjusted under 35 U.S.C. 154(b) by 582 days.

(21) Appl. No.: 14/836,544

(22) Filed: Aug. 26, 2015

(65) Prior Publication Data

US 2015/0359686 A1    Dec. 17, 2015

(51) Int. Cl.
| | |
|---|---|
| A61F 13/47 | (2006.01) |
| A61F 13/505 | (2006.01) |
| A61F 13/15 | (2006.01) |
| A61F 13/45 | (2006.01) |
| A61F 13/537 | (2006.01) |
| A61F 13/512 | (2006.01) |
| A61F 13/495 | (2006.01) |
| A61F 13/84 | (2006.01) |

(52) U.S. Cl.
CPC ...... *A61F 13/505* (2013.01); *A61F 13/15723* (2013.01); *A61F 13/15756* (2013.01); *A61F 13/45* (2013.01); *A61F 13/495* (2013.01); *A61F 13/512* (2013.01); *A61F 13/537* (2013.01); *A61F 13/84* (2013.01); *A61F 2013/15048* (2013.01); *A61F 2013/15715* (2013.01); *A61F 2013/53782* (2013.01); *Y10T 156/1057* (2015.01)

(58) Field of Classification Search
CPC .... A61F 13/474; A61F 13/495; A61F 13/505; A61F 13/512; A61F 13/537
See application file for complete search history.

(56) References Cited

U.S. PATENT DOCUMENTS

| | | | |
|---|---|---|---|
| 4,480,000 A | | 10/1984 | Watanabe et al. |
| 4,536,181 A | * | 8/1985 | Cook ............... A61F 13/474 604/387 |
| 4,597,759 A | * | 7/1986 | Johnson ............ A61F 13/474 604/385.16 |
| 4,626,254 A | | 12/1986 | Widlund et al. |

(Continued)

FOREIGN PATENT DOCUMENTS

WO    WO0153435    7/2001

OTHER PUBLICATIONS

Omli, R. et al, "Pad per day usage, urinary incontinence and urinary tract infections in nursing home residents", Oxford Univ on behalf of British Geriatrics Society, Internet article http://www.ageing.oxfordjournals.org, (Jul. 14, 2010).

*Primary Examiner* — Kathryn E Ditmer
(74) *Attorney, Agent, or Firm* — McHale & Slavin, P.A.

(57) ABSTRACT

An absorbent article for personal hygiene is disclosed with an absorbent core sealed between a liquid impermeable garment-side liner and a liquid permeable body-side cover together with an attached bacterial isolation pad, consisting of an absorbent layer sealed between an extension of the liquid impermeable garment-side liner and a liquid permeable topsheet which can be positioned to overlay the anal region of the body-side cover. A detachable bacterial isolation pad from the absorbent article and from the body-side cover is provided. Hygienic gripping tabs at the front-facing end of the absorbent article and at the rear-facing end of the bacterial isolation pad allow sanitary handling during removal of a soiled article.

13 Claims, 4 Drawing Sheets

(56) References Cited

U.S. PATENT DOCUMENTS

| | | | |
|---|---|---|---|
| 4,753,645 A | 6/1988 | Johnson | |
| 4,834,737 A | 5/1989 | Khan | |
| 4,880,417 A | 11/1989 | Yabrov et al. | |
| 5,207,663 A | 5/1993 | McQueen | |
| D368,519 S * | 4/1996 | Harrison | D24/125 |
| 5,704,929 A * | 1/1998 | Bien | A61F 13/474 |
| | | | 604/385.23 |
| 5,755,710 A | 5/1998 | Menard | |
| 5,891,125 A | 4/1999 | Plumley | |
| 5,941,863 A | 8/1999 | Guidotti et al. | |
| 5,947,949 A | 9/1999 | Inoue et al. | |
| 5,990,376 A | 11/1999 | Inoue et al. | |
| 6,060,637 A | 5/2000 | Bitowft et al. | |
| 6,083,602 A | 7/2000 | Caldwell et al. | |
| 6,107,539 A | 8/2000 | Palumbo et al. | |
| 6,117,524 A | 9/2000 | Hisanaka et al. | |
| 6,149,636 A | 11/2000 | Roe et al. | |
| 6,152,907 A | 11/2000 | Widlund et al. | |
| 6,177,606 B1 | 1/2001 | Etheredge et al. | |
| 6,186,991 B1 | 2/2001 | Roe et al. | |
| 6,213,991 B1 | 4/2001 | Kling et al. | |
| 6,238,379 B1 | 5/2001 | Keuhn, Jr. et al. | |
| 6,287,286 B1 | 9/2001 | Akin et al. | |
| 6,423,044 B1 | 7/2002 | Roe et al. | |
| 6,468,256 B1 | 10/2002 | Mishima | |
| 6,492,574 B1 | 12/2002 | Chen et al. | |
| 6,524,290 B2 | 2/2003 | Motta et al. | |
| 6,566,575 B1 | 5/2003 | Stickels et al. | |
| 6,595,977 B1 | 7/2003 | Luizzi, Jr. et al. | |
| 6,610,039 B1 | 8/2003 | Wilhelm et al. | |
| 6,623,466 B1 | 9/2003 | Richardson | |
| 6,685,686 B2 | 2/2004 | Hermansson et al. | |
| 6,689,114 B2 * | 2/2004 | Bouchard | A61B 10/0045 |
| | | | 600/573 |
| 6,726,668 B2 | 4/2004 | Underhill et al. | |
| 6,840,925 B2 | 1/2005 | Mishima et al. | |
| 6,881,206 B2 | 4/2005 | Underhill et al. | |
| 6,911,573 B2 | 6/2005 | Chen et al. | |
| 7,150,731 B2 | 12/2006 | Cazzato et al. | |
| 7,160,278 B2 | 1/2007 | Mizutani et al. | |
| 7,195,619 B2 | 3/2007 | Manasek | |
| 7,402,722 B2 | 7/2008 | Hill et al. | |
| 7,553,303 B2 | 6/2009 | Speak | |
| 7,598,428 B2 | 10/2009 | Gustaysson et al. | |
| 7,632,259 B2 | 12/2009 | Elfstrom et al. | |
| 7,670,324 B2 | 3/2010 | LaVon et al. | |
| 7,678,093 B2 | 3/2010 | Nordness et al. | |
| 7,686,792 B2 | 3/2010 | Bell et al. | |
| 7,695,460 B2 | 4/2010 | Wada et al. | |
| 7,722,587 B2 | 5/2010 | Suzuki et al. | |
| 7,749,211 B2 | 7/2010 | Van Gompel et al. | |
| 7,772,455 B1 | 8/2010 | Roe et al. | |
| 7,785,310 B2 | 8/2010 | Sakano et al. | |
| 7,790,947 B2 | 9/2010 | Hill et al. | |
| 7,858,842 B2 | 12/2010 | Komatsu et al. | |
| 7,943,158 B2 | 5/2011 | Nelson et al. | |
| 7,947,292 B2 | 5/2011 | Besemer et al. | |
| 7,993,316 B1 | 8/2011 | Fullman | |
| 8,016,803 B2 | 9/2011 | Mueller et al. | |
| 8,029,483 B2 | 10/2011 | Bonelli et al. | |
| 8,044,257 B2 | 10/2011 | Song | |
| 8,079,994 B2 | 12/2011 | Richlen et al. | |
| 8,082,636 B2 | 12/2011 | Miyamoto et al. | |
| 8,088,967 B2 | 1/2012 | Underhill et al. | |
| 8,110,215 B2 | 2/2012 | Koenig et al. | |
| 8,152,787 B2 | 4/2012 | Faulks et al. | |
| 8,987,543 B1 * | 3/2015 | Watson | A61B 5/208 |
| | | | 604/361 |
| 2002/0058917 A1 | 5/2002 | Hisanaka et al. | |
| 2002/0072725 A1 | 6/2002 | Kolby-Falk | |
| 2002/0087132 A1 | 7/2002 | Samuelsson | |
| 2002/0123729 A1 | 9/2002 | Ewick-Sonntag et al. | |
| 2002/0173761 A1 | 11/2002 | Roe | |
| 2003/0093045 A1 | 5/2003 | Erdman | |
| 2003/0120228 A1 | 6/2003 | Koenig et al. | |
| 2003/0125694 A1 * | 7/2003 | Motta | A61F 13/474 |
| | | | 604/385.04 |
| 2003/0163104 A1 | 8/2003 | Tears et al. | |
| 2004/0039362 A1 | 2/2004 | Roe et al. | |
| 2004/0082930 A1 | 4/2004 | Bast et al. | |
| 2004/0147889 A1 | 7/2004 | Roe et al. | |
| 2004/0193130 A1 | 9/2004 | Fima et al. | |
| 2004/0249356 A1 * | 12/2004 | Bell | A61F 13/474 |
| | | | 604/385.16 |
| 2005/0182376 A1 | 8/2005 | Fleming | |
| 2006/0036223 A1 | 2/2006 | Baldwin et al. | |
| 2006/0142729 A1 | 6/2006 | Sivilich et al. | |
| 2007/0088304 A1 | 4/2007 | Sakano et al. | |
| 2007/0232167 A1 | 10/2007 | Hill et al. | |
| 2007/0255244 A1 * | 11/2007 | Olsson | A61F 13/505 |
| | | | 604/385.14 |
| 2008/0058754 A1 | 3/2008 | Lavon et al. | |
| 2008/0248087 A1 | 10/2008 | Hill et al. | |
| 2008/0300557 A1 | 12/2008 | Forsgren Brusk et al. | |
| 2009/0030390 A1 | 1/2009 | Hammons et al. | |
| 2009/0030391 A1 | 1/2009 | Hammons et al. | |
| 2009/0076472 A1 | 3/2009 | Goldwasser et al. | |
| 2009/0131899 A1 | 5/2009 | Ross | |
| 2009/0247972 A1 | 10/2009 | Fleming | |
| 2009/0287177 A1 | 11/2009 | Tatsukawa et al. | |
| 2010/0036338 A1 | 2/2010 | Hammons et al. | |
| 2010/0036349 A1 | 2/2010 | Hammons et al. | |
| 2010/0145296 A1 | 6/2010 | Kudo et al. | |
| 2010/0290948 A1 | 11/2010 | Song | |
| 2010/0312210 A1 | 12/2010 | Schuehle (nee Hoffmann) et al. | |
| 2011/0125117 A1 | 5/2011 | Kudo | |
| 2011/0168318 A1 | 7/2011 | Nilsson et al. | |
| 2014/0188065 A1 * | 7/2014 | Defrancesco | A61F 13/4758 |
| | | | 604/370 |
| 2017/0239101 A1 * | 8/2017 | Lee | A61F 13/4704 |

* cited by examiner

ABSORBENT ARTICLE WITH A BACTERIAL ISOLATION PAD AND HYGIENIC GRIPPING TABS

CROSS REFERENCE TO RELATED APPLICATION

In accordance with 37 C.F.R. 1.76, a claim of priority is included in an Application Data Sheet filed concurrently herewith. Accordingly, the present invention claims priority as a continuation-in-part of U.S. patent application Ser. No. 13/495,624, entitled "ABSORBENT ARTICLE WITH A BACTERIAL ISOLATION PAD AND HYGIENIC GRIPPING TABS", filed Jun. 13, 2012, the contents of which is herein incorporated by reference in its entirety.

FIELD OF THE INVENTION

The present invention relates generally to an improvement to a personal hygiene absorbent article used as an incontinence pad, pantiliner, diaper, or other absorbent undergarment. More specifically, the present invention pertains to absorbent articles designed to absorb urinary liquids and limit bacterial contamination from the anus of an individual to the urethra and also to provide hygienic grips for secure and sanitary handling of a soiled article.

BACKGROUND OF THE INVENTION

Urinary tract infections (UTIs) are the second most common type of infection in the body, most of which are caused by bacteria that live in the bowel. Women are especially susceptible because of the short distance bacteria have to travel from the anus to the urethra. Fecal drainage, improper cleansing after evacuation and extended wear of a wet absorbent pad or undergarment are all considered risk factors for a UTI. A Norwegian study titled, "Pad per day usage, urinary incontinence and urinary tract infections in nursing home residents," published online in July 2010 on behalf of the British Geriatrics Society, concluded that the use of absorbent pads is associated with an increased risk of developing UTIs.

Women with urinary incontinence rely on absorbent pads, pantiliners and undergarments, which are readily available and simple to use. These absorbent articles use a continuous absorbent core extending to the front and rear from the point of urinary insult, allowing a larger area for absorption of urine, but also providing a path for migration of anal bacteria to the urethra along a dampened topsheet or urine-soaked absorbent core.

DESCRIPTION OF THE PRIOR ART

Omli, Ragnhild et al., "Pad per day usage, urinary incontinence and urinary tract infections in nursing home residents," published online on Jul. 14, 2010 by Oxford University Press on behalf of the British Geriatrics Society in ageing.oxfordjournals.org. This article discusses the results of a study performed in six nursing homes. The study concluded that the residents of nursing homes who used absorbent pads were at an increased risk of developing urinary tract infections (UTIs).

U.S. Pat. No. 7,943,158 discloses a means to produce antimicrobial activity in fabric material. The means reduces the microbial content on an article in close proximity to an animal body by providing molecular iodine to the stabilized reagents when at least two reactants are activated by aqueous and/or alcohol materials. Use in a diaper is mentioned, but no other design changes are disclosed.

In response to concerns of bacterial contamination, barrier webs impermeable or toxic to microorganisms disclosed in U.S. Pat. No. 6,083,602 and fibers which trap bacteria disclosed in U.S. Pat. No. 7,947,292 have been created for use in absorbent hygiene products such as diapers, napkins, and tissues. Use of the fabrics in diapers and other absorbent articles is mentioned, but no other design changes are disclosed.

U.S. Pat. No. 6,083,602 discloses a web material which has been treated with a curable shear thinned thixotropic polymer composition. The material is then substantially impermeable to liquids, permeable to gases, and impermeable to microorganisms.

U.S. Pat. No. 7,947,292 discloses a hygiene product containing fibrous material for removing or inactivating microbes. This is accomplished by the fibrous material containing functional groups capable of interacting with bacteria cell walls.

From these three patents, it appears that the only change foreseen to existing absorbent articles is use of their fabric in existing designs or addition of a fabric covering. How these bacteria control fabrics are incorporated into commonly used incontinence products in the general population, where cost, comfort, and performance are major factors, remains to be seen.

Some absorbent articles, such as U.S. Pat. No. 5,755,710 and U.S. Published Patent Application No. 2003/0093045, have a defined urine strike window, intended to provide leakage protection. This feature does not limit migration of anal bacteria as fecal drainage trickles along the liquid impervious topsheet down into the strike window. To avoid this occurrence, someone skilled in the art may add an entry zone for fecal insult in the anal region of the article. Unfortunately, this access then establishes a direct path for migration of anal bacteria to the urethra through the continuous absorbent core when it becomes saturated with urine, as in a regular incontinence pad.

U.S. Pat. No. 5,755,710 discloses an absorbent article for use in the perineal area of the body. The article has an absorbent core which has an upper body facing surface, a lower garment facing surface, first and second longitudinal sides, and first and second transverse ends. A body fluid impervious sealing wrapper having upper and lower portions each having longitudinally and transversely extending edges along which the portions are joined is formed around the absorbent core so as to enclose at least the entirety of the garment facing surface, the longitudinal sides, and the transverse ends, thereby forming a seal. The article has a centrally disposed opening in the upper portion of the sealing wrapper thus forming a window on the body facing surface of the absorbent core that exposes it to fluid flow.

U.S. Published Patent Application No. 2003/0093045 discloses an absorbent article which provides leakage protection and protection for the skin of the individual using the article. The article includes a selectively-permeable top sheet, a substantially impermeable back sheet, and an absorbent core located between the top sheet and the back sheet. The top sheet has a treated hydrophilic zone and an untreated hydrophobic zone.

Sanitary handling of urine-soaked incontinence pads is also a concern. Today's commonly used incontinence pads are designed to be gripped by the peripheral fringes for removal. While the back sheet of the pad is liquid impervious, the liquid pervious top sheet on the top side of the fringe allows urine to seep onto the top side of the fringe.

U.S. Pat. No. 6,595,977 provides a tape tab, which extends from the sides or ends of an absorbent article to provide a hygienic means of removing the article. Since the primary function of the tape tab is to adhesively maintain the position of an absorbent article, all claims are specifically for an adhesive tape tab. This design not only requires the user to detach the tab from the user's garment before removal, but also extends the gripping point away from the body of the absorbent article, contributing unwanted movement to a urine-soaked article during removal and disposal.

U.S. Pat. No. 7,553,303 is the applicant's prior patent which discloses an undergarment having at least one aperture in the crotch region for the removal of and insertion of absorbent pads.

What is lacking in the art is an absorbent article for an incontinent person that physically separates anal bacteria from urine absorbed by the article, without reducing the absorption area of the article or requiring the use of special fibers, barrier webs, or other costly or special manufacturing processes. Also lacking in the art is gripping points to allow quick and easy hygienic removal of a fully saturated incontinence pad.

SUMMARY OF THE INVENTION

An absorbent article for use as an incontinence pad or pantiliner includes a bacterial isolation pad which is affixed atop an extended portion of the incontinence pad's garment side liner. A U-shaped cut through the garment-side liner around the front facing perimeter of the bacteria isolation pad allows the bacterial isolation pad to be positioned to overlay the rear portion of the body side cover to block bacteria in the anal region from contacting the urine receiving portion of the article. A liquid impermeable gripping tab is attached at the front facing end of the incontinence pad and the rear facing end of the bacterial isolation pad to provide hygienic removal of the article. Horizontal perforations allow tearing to remove strips of the garment side liner which attach the bacterial isolation pad to the incontinence pad.

In a second embodiment of the present invention, the incontinence pad of the first embodiment with rectangular-shaped incontinence and bacterial isolation pads is disclosed. The bacterial isolation pad is contained between an extension of the garment-side liner and the body-side cover from the rear-facing end of the incontinence pad.

In a third embodiment, an absorbent article for use as an absorbent undergarment, diaper or pull-up with an attached bacterial isolation pad is disclosed. A bacterial isolation pad is contained between an extension of the garment-side liner and the body-side cover at the rear-facing end of an absorbent crotch member.

In a fourth embodiment, the absorbent undergarment of the third embodiment with an attached bacterial isolation pad is disclosed. All aspects are the same, except that, as in the first embodiment, the bacterial isolation pad is affixed atop the body-facing side of the extended liquid impermeable garment-side liner and is enclosed by a separate liquid permeable top sheet.

Accordingly, it is an objective of the present invention to provide an absorbent article for use as an incontinence pad, pantiliner, or diaper-type undergarment. A bacterial isolation pad is secured to and overlays a rear section of the incontinence pad on the side of the incontinence pad which faces a user.

It is a further objective of the present invention to prevent bacteria from the anal region of an individual from coming in contact with urine and causing urinary tract infections.

It is yet another objective of the present invention to provide an absorbent article for use as an incontinence pad or pantiliner which includes a gripping tab secured to the front-facing end of the incontinence pad or pantiliner.

It is a still further objective of the present invention to provide an absorbent article for use as an incontinence pad or pantiliner which includes a gripping tab secured to a bacterial isolation pad to provide hygienic removal and disposal of the isolation pad.

It is a still further objective of the present invention to provide an absorbent article for use as an incontinence pad or pantiliner. A bacterial isolation pad is secured to and overlays a rear section of the incontinence pad on the side of the incontinence pad which faces a user.

It is a still further objective of the present invention to provide an undergarment, a diaper, or a pull-up with a bacterial isolation pad which prevents bacteria from the anal region of an individual from coming in contact with urine from the same individual.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1:
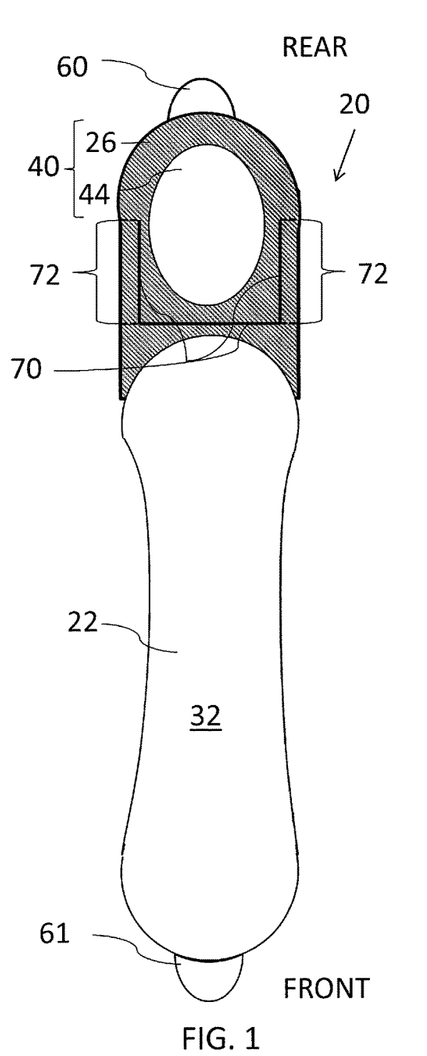
FIG. 1 is a plan view of the body facing side of an embodiment used as an incontinence pad with an attached bacterial isolation pad.
Figure 2:
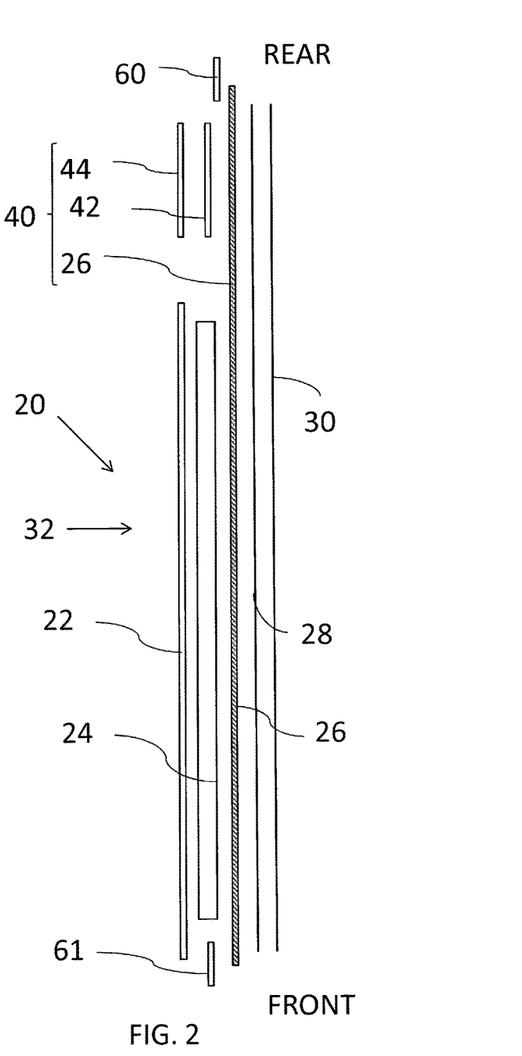
FIG. 2 is a longitudinal cross-section of the embodiment of FIG. 1, with edges not shown bonded.

FIGS. 1-8, which are now referenced, illustrate the present invention and the manner in which it is assembled. A preferred embodiment of the present invention is illustrated in FIGS. 1 and 2. In this embodiment, an absorbent article 20 is illustrated. In this preferred embodiment, the absorbent article is an incontinence pad 32 with an attached bacterial isolation pad 40. The incontinence pad is used by an individual whenever there is a chance that bodily fluids and/or wastes can or will be discharged unexpectedly or at an inopportune time. One of the main uses or purposes of an incontinence pad is to absorb and retain fluids discharged from an individual so that the fluids cannot be passed onto clothing or other materials which would result in an unsightly stain or damage of the clothing. The incontinence pad 32 includes an absorbent core 24 which absorbs fluids. A permeable body-side cover or layer 22 is secured to an upper surface of the core 24, as illustrated in FIG. 2. The upper surface is defined as the surface of the core 24 which is closest to the body of an individual when the pad 32 is in use. The permeable body-side cover 22 is formed from a fluid permeable material. In the preferred embodiment, urine from an individual passes through the body-side cover 22 and is absorbed into the core 24. The core 24 is made from a material which will absorb and retain fluids. Thus, the urine is retained in the core 24 so that the urine will not move or be transported onto an individual's clothing or other areas of an individual's body. This prevents wetting and unsightly stains on garments.

Secured to the lower surface or underside of the core 24 is liner or fluid impermeable layer 26. In a preferred embodiment, the liner 26 is a garment side liner. The fluid impermeable layer 26 is constructed and arranged to prevent any fluids from passing from the core 24 onto a garment or article of clothing, (not shown). The fluid impermeable layer 26 has an adhesive strip 28 secured to a first side, as illustrated in FIG. 2. The adhesive strip 28 is employed to both secure the incontinence pad to a garment or an article of clothing and to prevent the incontinence pad from moving when in use. Normally the incontinence pad 32 is secured to an undergarment such as panties. As a result of an individual moving, walking, sitting, etc. the panties will move relative to the individual's body. If the incontinence pad 32 were not secured to the panties, it would be moved out of its desired or preferred position as a result of the individual's movement. The desired position of the incontinence pad 32 is adjacent the lower portion of an individual's body where fluids are released or expelled, the urethra, the vagina and the anus.

In a preferred embodiment, the incontinence pad 32 has a narrow central portion located between the wider rounded distal end portions. The dimensions of this embodiment of the incontinence pad 32 are 10 inches long, along a centerline of the pad, 3.5 inches wide, at the widest portion of the pad, and 2.5 inches wide, at the narrowest or central portion of pad 32. Dimensions in these descriptions do not include fringes around the periphery of the incontinence pad 20 or bacterial isolation pad 40 after sealing the absorbent core 24 or absorbent layer 42.

A bacterial isolation pad 40 is secured to one end of the incontinence pad 32, as illustrated in FIGS. 1 and 2. The end at which the bacterial isolation pad 40 is secured is considered to be the rear or back end of the incontinence pad 32. When the incontinence pad 32 is placed against an individual's body, the rear end of the incontinence pad is located at or toward the rear side of the individual's body. The ideal position of the bacterial isolation pad 40 is adjacent an individual's anus. The bacterial isolation pad 40 includes a fluid absorbent layer or pad 42 which is from a material which will absorb and retain fluids. A fluid permeable topsheet or layer 44 is secured to a first side of said bacterial isolation pad 40. Fluids discharged from an individual's anus pass through the top sheet 44 and into pad 42 where they are retained. The second side of said layer or paid 42 is secured to the incontinence pad's 32 impermeable backsheet or layer 26.

Figure 3:
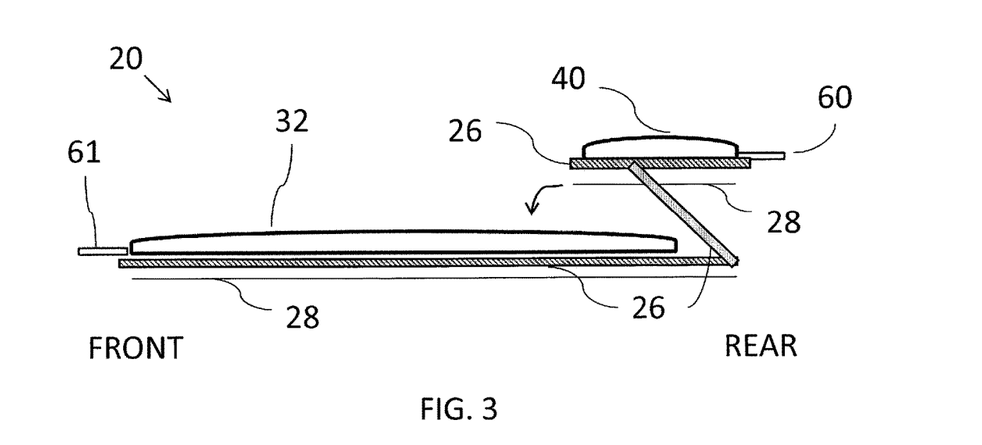
FIG. 3 is a side view of the embodiment in FIG. 1, with the adhesive peel strip removed. The attached bacterial isolation pad is raised to overlay the rear of the incontinence pad.

As illustrated in FIGS. 1 and 3, the bacterial isolation pad 40 is oval shaped. However, any other shape may be employed. The only criteria are that the bacterial isolation pad 40 trap and retain fluids discharged from the anus of an individual. This prevents these fluids from coming into contact with urine and/or other fluids discharged from an individual. Intermixing of anal fluids and urine may result in a urinary tract infection. The present invention prevents this.

A 3.5 inch wide garment-side liner 26 at the rear-facing portion of the incontinence pad 32 extends 4 inches measured from the tip of the incontinence pad 32 to the tip of a rounded end. A bacterial isolation pad 40, consisting of a 2.5 inch wide and 3.0 inch long ovate absorbent layer 42 enclosed by an ovate liquid permeable top sheet 44, is affixed atop the body-facing side of the liquid impermeable garment-side liner 26. The front-facing tip of the ovate absorbent layer 42 is placed 0.75 inches from the rear-facing tip of the absorbent core 24 and is centered horizontally on the garment-side liner 26. A 3 inch wide and 1.25 inch long U-shaped cut 70 through the garment-side liner 26 brackets the bacterial isolation pad 40 0.25 inches from its front-facing edge.

FIG. 3 illustrates the bacterial isolation pad 40 extending outward from the substantially U-shaped cut 70 forming a channel in the garment side liner as the underlying garment-side liner 26 is raised and moved forward to overlay the bacterial isolation pad 40 onto the rear portion of the incontinence pad 32. The substantially U-shaped channel is integrally formed between the interior of said fluid impermeable side liner 26 and said body side cover 22. This places the top sheet 44 of the bacterial isolation pad 40 in contact with the anal region of the wearer, to absorb and isolate anal bacteria.

Horizontal perforations 72 in the garment-side liner 26 are made at 4 locations between the ends of each 1.25 inch side cut 70 and the outside edge of the garment-side liner 26. The perforations 72 allow the user to tear off the outside strips of the garment-side liner 26 after the bacterial isolation pad 40 has been affixed atop the incontinence pad 32 to detach the bacterial isolation pad 40 from the incontinence pad 32. This may also increase comfort during use.

Gripping tabs 60 and 61 are secured to at least one end of the pad 32, as illustrated in FIGS. 1 and 2. The gripping tabs 60 and 61 provide hygienic grips for secure and sanitary handling of the incontinence pad 32. The gripping tabs 60 and 61 are made from a liquid impervious material in order to provide a firm gripping surface for an individual removing a soiled incontinence pad. In a preferred embodiment, the gripping tabs 60 and 61 are arched shaped. They are 0.75 inches high and 1.5 inches at their widest point. The tabs 60 and 61 are preferably secured at the center portions of the ends of the incontinence pad 32.

The liquid impermeable garment-side liner 26 has one or more tracks of releasable garment adhesive 28 placed along the longitudinal centerline of the downward-facing surface for releasable attachment of the incontinence pad 32 to a garment. A releasable or removable adhesive peel strip 30 is designed to be removed by the customer just prior to positioning and attaching the bacterial isolation pad 40 onto the rear portion of the incontinence pad 32 and then attaching the incontinence pad 32 to the crotch region of an undergarment (not shown). The releasable adhesive peel strip 30 is generally slightly larger than the overall dimension of the area of attachment adhesive 28 for ease of manufacture and to allow a gripping edge for ease of removal.

The body-side cover 22 and fluid impermeable layer 26 can be made from materials commonly used in the industry to produce fluid permeable or fluid impermeable materials. Additionally, these elements can be made from a material and treated or coated with material(s) to render them fluid permeable or fluid impermeable. Woven or non-woven materials formed from natural or synthetic fibers and/or other materials can be employed to make these elements. Fluid impermeable layer 26 can be made from fluid impermeable materials such as, but not limited to, polyaminates, polymeric films such as polyethylene, polypropylene, polyester, cellophane, etc. or a bi-component film. Non-woven fabrics, impregnated fluid repellent paper, and other materials can also be used. Outer edges of the body-side cover 22 and the garment side liner 26 are sealed together to contain the incontinence pad 32 absorbent core 24 and the bacterial isolation pad 40 absorbent layer 42. These edges can be joined by pressure sensitive adhesives, heat sensitive adhesives, ultrasonics, or other known joining applications which prevent fluid discharge beyond these outer edges. The sealing of these edges may be continuous, discontinuous, or staggered.

Absorbent core 24 is illustrated as being formed from a single absorbent layer. However, multiple absorbent and/or wicking layers can be employed to form the absorbent core 24. The materials from which the absorbent core 24 is made will determine the fluid capacity of the core 24. Pulp, super-absorbent polymers, and other organic and inorganic materials well known in the art are illustrative of materials which are commonly employed for their absorbent properties.

In a preferred embodiment of the present invention, the bacterial isolation pad 40 is secured to the outer periphery of the incontinence pad 32 of the overlay areas. It can also be directly bonded to the body side cover 22 directly below or attached in various configurations or locations. The size, shape, construction, and configuration of the bacterial isolation pad 40 may be varied to accommodate various absorbency, placement, and design criteria.

A top sheet 44 and absorbent core 24 may cover a larger or smaller area of the liquid impermeable garment-side liner 26. A top sheet 44 may be of the same materials as the body-side cover 22 described above, or a treated fabric, like that described in U.S. Pat. No. 7,943,158, may be used. Microorganism barrier webs, like those presented in U.S. Pat. No. 6,083,602 or bacteria trapping fibrous materials, of the type presented in U.S. Pat. No. 7,947,292, may also be used. Likewise, an absorbent layer 42 of the bacterial isolation pad 40 may be of the same materials as the absorbent core 24 of an incontinence pad 32 or one or more sheets of a bacteria containment product, as described for a top sheet 44.

It is foreseeable that one or more layers of bacteria trapping fibrous materials and/or microorganism barrier webs may be used as a combination garment-side liner 26, absorbent core 42 and top sheet 44, with a liquid impervious incontinence pad 32 interface.

Figure 4:
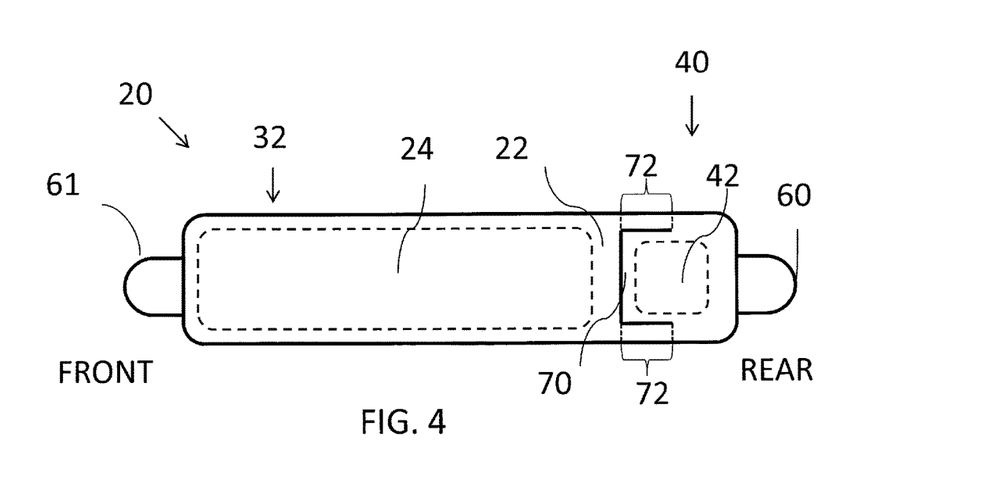
FIG. 4 is a plan view of the body facing side of an embodiment used as an incontinence pad with an attached bacterial isolation pad.
Figure 5:
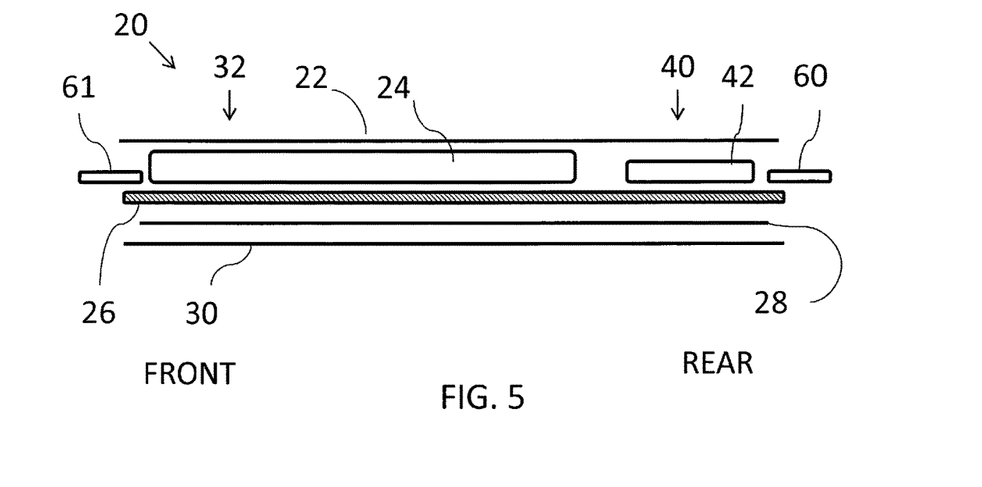
FIG. 5 is a longitudinal cross section of the embodiment in FIG. 4, with edges not shown bonded.

A second embodiment discloses where the absorbent article 20 of the first embodiment shown in FIG. 1, FIG. 2, and FIG. 3 is a rectangular incontinence pad 32. The absorbent article 20 is 10 inches long and 3.5 inches wide, with an attached rectangular bacterial isolation pad 40, 3 inches long and 2.5 inches wide as shown in FIG. 4 and FIG. 5. The absorbent layer 42 of the bacterial isolation pad 40 is contained between a 3.5 inch wide and 4 inch long extension of the garment-side liner 26 and the body-side cover 22 from the rear-facing end of the absorbent core 24 to a rectangular end. The garment-side liner 26 and the body-side cover 22 are joined in all parts of the extension surrounding the bacterial isolation pad 40. A 3 inch wide and 1.25 inch long U-shaped cut 70 through the joined garment-side liner 26 and the body-side cover 22 brackets the bacterial isolation pad 40 0.25 inches from its front-facing and side edges. Horizontal perforations 72 in the joined garment-side liner 26 and the body-side cover 22 are made as described in the first embodiment. All other aspects including adhesion, materials, joining methods and hygienic gripping tabs for the bacterial isolation pad 40 and the incontinence pad 32 are as described in the first embodiment.

Figure 6:
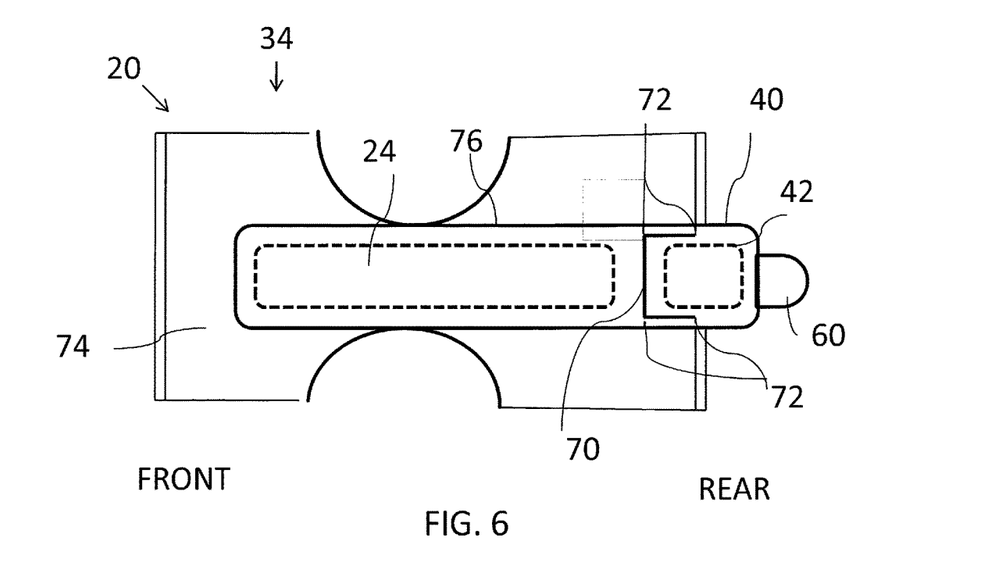
FIG. 6 is a plan view of the body facing side of an embodiment used as an absorbent undergarment with a bacterial isolation pad on the unattached end of the absorbent crotch member.
Figure 7:
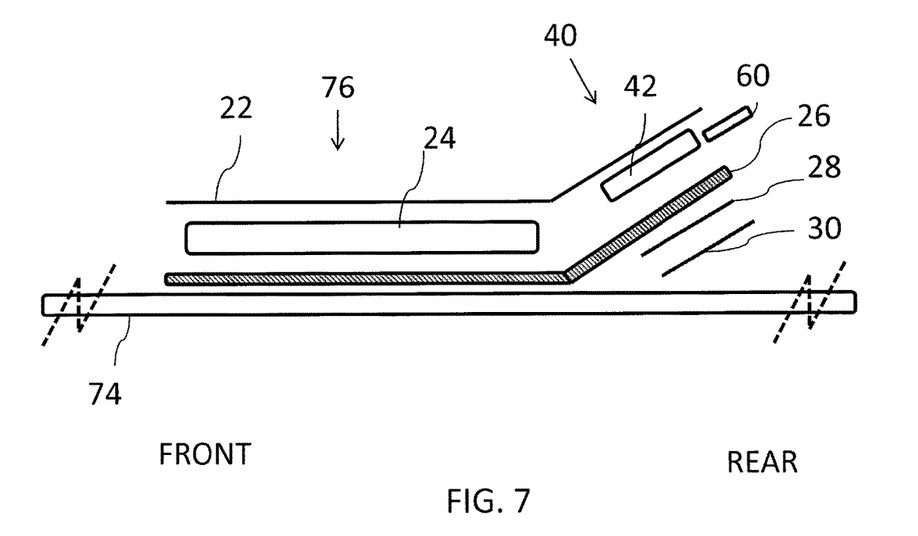
FIG. 7 is a longitudinal cross section of the crotch member and the bacterial isolation pad of the embodiment in FIG. 6.
Figure 8:
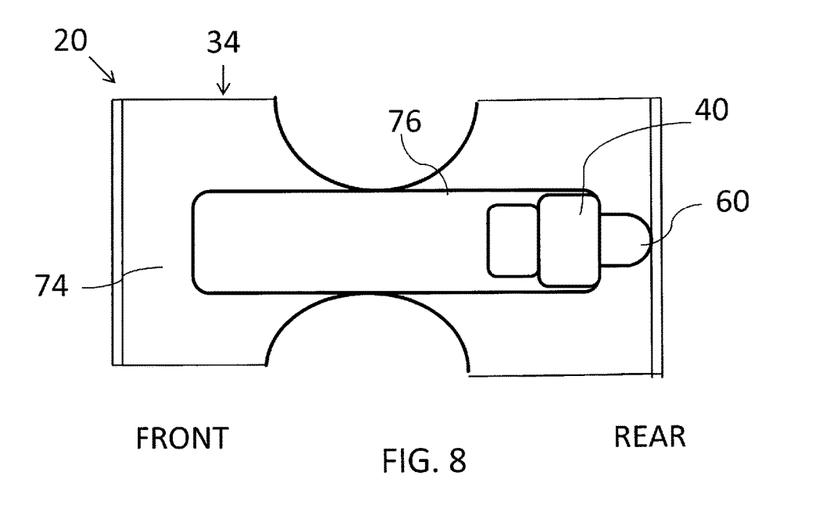
FIG. 8 is a plan view of the body facing side of the embodiment in FIG. 6, with the bacterial isolation pad overlaying the anal region of the crotch member of the undergarment and perforated sides attaching the bacterial isolation pad removed.

A third embodiment is disclosed in FIG. 6, FIG. 7 and FIG. 8, where an absorbent article 20 is presented as an absorbent undergarment 34 with a bacterial isolation pad 40 attached to an extension of the crotch member 76 for placement in the anal region of the absorbent portion of the crotch member 76. The garment 34 may also be a diaper or pull-up. The garment 34 is for the lower torso and can be constructed from any suitable material to provide a disposable diaper-type garment. The garment 34 also includes a body panel 74 and an absorbent crotch member 76. The body panel 74 has a front panel and a rear panel, with a crotch region there between. The absorbent crotch member 76 consists of a liquid permeable body-side cover 22, a liquid impermeable garment-side liner 26 with a rectangular urine-receiving absorbent core 24, 16 inches long and 4 inches wide, contained therein. The portion of the garment-side liner 26 containing the absorbent core 24 is centered and attached to the body panel 74 from front to back through the crotch region, using joining methods discussed in the first embodiment. The body panel 74 extends 3 inches beyond each end of the attached portion of the absorbent crotch member 76 for the waist area.

The 3 inch wide and 4 inch long absorbent layer 42 of a bacterial isolation pad 40 is contained between a 4 inches wide and 5 inches long rectangular extension of the garment-side liner 26 and the body-side cover 22 from the rear-facing end of the absorbent core 24 of the crotch member 76. The front-facing end of the absorbent layer 42 is placed 0.75 inches from the rear-facing end of the absorbent core 24. The garment-side liner 26 and the body-side cover 22 are joined in all parts of the extension surrounding the absorbent layer 42. A 3.5 inch wide and 2 inch long U-shaped cut 70 through the joined garment-side liner 26 and the body-side cover 22 brackets the bacterial isolation pad 40 0.25 inches from its front-facing and side edges.

As illustrated in FIG. 7, the extended portion of the crotch member 76 garment-side liner 26 containing the bacterial isolation pad 40 is not attached to the body panel 74 of the garment 34. The unattached portion of the liquid impermeable garment-side liner 26 has one or more tracks of releasable garment adhesive 28 placed along the longitudinal centerline of the downward-facing surface for releasable attachment to the body-side cover 22. A releasable or removable adhesive peel strip 30 is designed to be removed by the customer just prior to positioning and attaching the bacterial isolation pad 40 onto the rear portion of the crotch member 76. The releasable adhesive peel strip 30 is generally slightly larger than the overall dimension of the area of attachment adhesive 28 for ease of manufacture and to allow a gripping edge for ease of removal.

Horizontal perforations 72 in the garment-side liner 26 and the body-side cover 22 are made at 4 locations between the ends of each 2 inch side cut 70 and the outside edge of the garment-side liner 26. Functions of the perforations 72 are as described in the first embodiment. FIG. 8 illustrates the bacterial isolation pad 40 overlaying the anal region of the absorbent crotch member 76 with the perforated portions of the garment-side liner 26 removed. An arched gripping tab 60, 0.75 inches high and 1.5 inches at its widest point, is centered at the rear-facing end of the bacterial isolation pad 40 for secure and sanitary handling.

A fourth embodiment, which is not illustrated, is disclosed where the absorbent article 20 of the third embodiment is an absorbent undergarment 34, shown in FIG. 6, FIG. 7 and FIG. 8, with an attached bacterial isolation pad 40. All aspects are the same, except that, similar to the first embodiment, the absorbent layer 42 of the bacterial isolation pad 40 is affixed atop the body-facing side of the extended liquid impermeable garment-side liner 26 and is enclosed by a separate liquid permeable top sheet 44.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An absorbent article for protection against bacterial contamination comprising:
    a continuous fluid impermeable liner having a front section, a rear section, a first longitudinal side, a second longitudinal side, a body-facing surface and a garment-facing surface;
    a body side cover layer;
    a first absorbent core positioned on said body-facing surface in said front section, said first absorbent core constructed and arranged for capturing urine;
    a second absorbent core positioned on said body-facing surface in said rear section; said second absorbent core spaced from said first absorbent core by a channel;
    a U-shaped cut extending through said liner in the region of said channel, said U-shaped cut bracketing said second absorbent core;
    a plurality of lines of perforations comprising at least a first line extending from one side the U-shaped cut to the first longitudinal side and a second line extending from the opposite side the U-shaped cut to the second longitudinal side;
    a first gripping tab attached to said rear section;
    whereby said second absorbent core and a portion of said liner are configured to be raised and moved towards said front section so as to overlay said first absorbent core while said liner remains continuous, said rear section of said liner and said second absorbent core configured to be removed by pulling said first gripping tab causing tearing along said perforations to avoid bacterial contamination by detaching said rear section from said front section.

2. The absorbent article of claim 1 comprising at least one gripping tab secured to said front section.

3. The absorbent article of claim 1 wherein said at least one gripping tab is constructed of a liquid impermeable material.

4. The absorbent article of claim 1 wherein said at least one gripping tab is arched shaped.

5. The absorbent article of claim 1 wherein said second absorbent core comprises an ovate absorbent layer.

6. The absorbent article of claim 1 wherein said second absorbent core comprises a rectangular absorbent layer.

7. An undergarment integrally formed with the absorbent article of claim 1.

8. A method of construction of an absorbent article for protection against bacterial contamination comprising:
    providing a continuous fluid impermeable liner having a front section, a rear section, a first longitudinal side, a second longitudinal side, a body-facing surface and a garment-facing surface;
    providing a body side cover layer;
    positioning a first absorbent core on said body-facing surface in said front section, said first absorbent core constructed and arranged for capturing urine;
    positioning a second absorbent core on said body-facing surface in said rear section, said second absorbent core spaced from said first absorbent core by a channel;
    forming a U-shaped cut extending through said liner in the region of said channel, said U-shaped cut bracketing said second absorbent core;
    forming a plurality of lines of perforations comprising at least a first line extending from one side the U-shaped cut to the first longitudinal side and a second line extending from the opposite side the U-shaped cut to the second longitudinal side;
    attaching at least one gripping tab to said liner;
    whereby said second absorbent core and a portion of said liner are configured to be raised and moved towards said front section so as to overlay said first absorbent core while said liner remains continuous, said rear section of said liner and said second absorbent core configured to be removed by pulling said at least one gripping tab causing tearing along said perforations to avoid bacterial contamination by detaching said rear section from said front section.

9. The method of construction of claim 8 wherein said at least one gripping tab is constructed of a liquid impermeable material.

10. The method of construction of claim 8 wherein said at least one gripping tab is arched shaped.

11. The method of construction of claim 8 wherein said second absorbent core comprises an ovate absorbent layer.

12. The method of construction of claim 8 wherein said second absorbent core comprises a rectangular absorbent layer.

13. A method of construction of a garment comprising:
performing the method of claim 8;
integrally attaching the absorbent article produced from the method of claim 8 to the crotch region of a garment configured to be worn on the lower torso of a wearer.

* * * * *